United States Patent
Lee

(10) Patent No.: US 7,639,236 B2
(45) Date of Patent: Dec. 29, 2009

(54) IMAGE SENSOR, OPTICAL POINTING DEVICE AND MOTION CALCULATING METHOD OF OPTICAL POINTING DEVICE

(75) Inventor: Bang-Won Lee, Yongin-si (KR)

(73) Assignee: Atlab Inc. (KR)

( * ) Notice: Subject to any disclaimer, the term of this patent is extended or adjusted under 35 U.S.C. 154(b) by 533 days.

(21) Appl. No.: 11/078,503

(22) Filed: Mar. 11, 2005

(65) Prior Publication Data

US 2005/0200600 A1 Sep. 15, 2005

(30) Foreign Application Priority Data

Mar. 11, 2004 (KR) .................. 10-2004-0016607

(51) Int. Cl.
*G06F 3/033* (2006.01)
*G09G 5/08* (2006.01)

(52) U.S. Cl. ................................... 345/166

(58) Field of Classification Search ......... 345/156–158, 345/162, 163, 166, 165
See application file for complete search history.

(56) References Cited

U.S. PATENT DOCUMENTS

| 4,663,535 A * | 5/1987 | Nakai et al. ........... 358/513 |
| 6,507,011 B2 * | 1/2003 | Ang ..................... 250/208.1 |
| 7,170,494 B2 * | 1/2007 | Park et al. .............. 345/166 |
| 2004/0095323 A1 * | 5/2004 | Ahn ....................... 345/166 |
| 2004/0119695 A1 * | 6/2004 | Lee ........................ 345/166 |

(Continued)

FOREIGN PATENT DOCUMENTS

JP 2003157145 5/2003

(Continued)

OTHER PUBLICATIONS

Machine translation of KR 1998-080492.*

(Continued)

*Primary Examiner*—Amr Awad
*Assistant Examiner*—Michael Pervan
(74) *Attorney, Agent, or Firm*—Cantor Colburn LLP

(57) ABSTRACT

An image sensor, an optical pointing device and a motion calculating method of the optical pointing device are disclosed. The optical pointing device includes an image sensor for obtaining and providing a surface image corresponding to a motion searching range; and an image processor for determining a direction and a length of an X axis and a Y axis of the motion searching range and a reference area to continuously obtain the surface image corresponding to the direction and length of the X axis and Y axis, obtaining a reference frame and a current frame using the continuously obtained surface image, setting a certain area of the reference frame corresponding to the direction and length of the X axis and Y axis of the reference area as the reference area, and calculating a correlation between the reference area and the sample frame, to thereby calculate motion. The image sensor can obtain the larger surface image in the X axis direction. Thus, even though the optical pointing device collects the image at a low sampling rate, there is an effect in that larger motion of the optical pointing device for the X axis direction can be calculated. This helps reduce the operating speed of the semiconductor to thereby reduce power consumption.

4 Claims, 12 Drawing Sheets

U.S. PATENT DOCUMENTS

2005/0060668 A9 * 3/2005 Lee et al. .................... 715/856
2005/0062720 A1 * 3/2005 Rotzoll et al. ............... 345/166

FOREIGN PATENT DOCUMENTS

| KR | 1998080492 | 11/1998 |
| TW | 460845 | 10/2001 |
| TW | 489275 | 6/2002 |
| TW | 535440 | 6/2003 |
| TW | 200301867 | 7/2006 |

OTHER PUBLICATIONS

Preliminary Notice of the First Office Action issued Apr. 11, 2008 in the corresponding Taiwanese Patent Application 094107089 including an English Translation thereof.

Search Report associated with the Preliminary Notice of the First Office Action issued Apr. 11, 2008.

Korean Office Action issued on Jul. 24, 2006.

* cited by examiner

FIG. 3
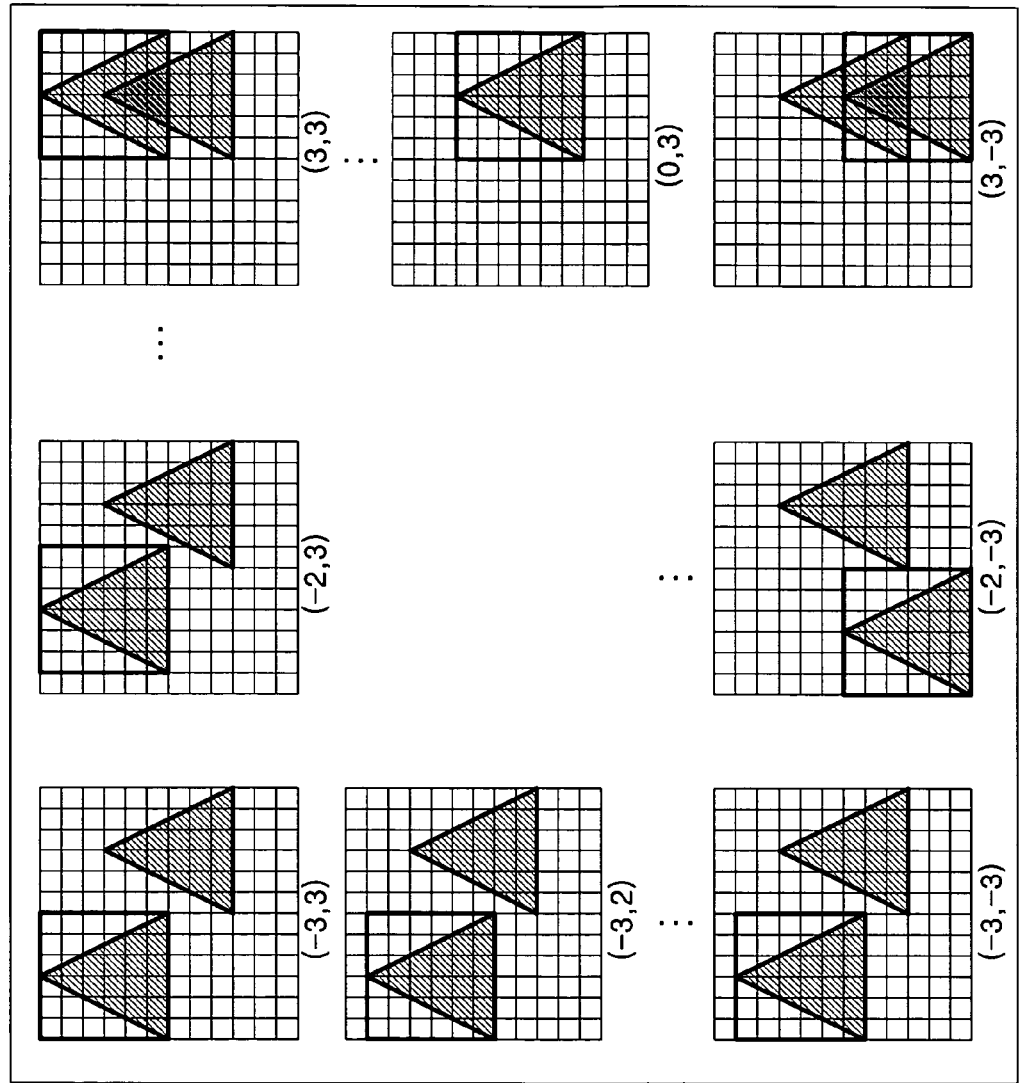
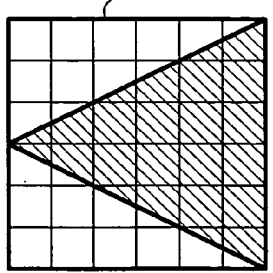

X PITCH < Y PITCH

FIG. 8A
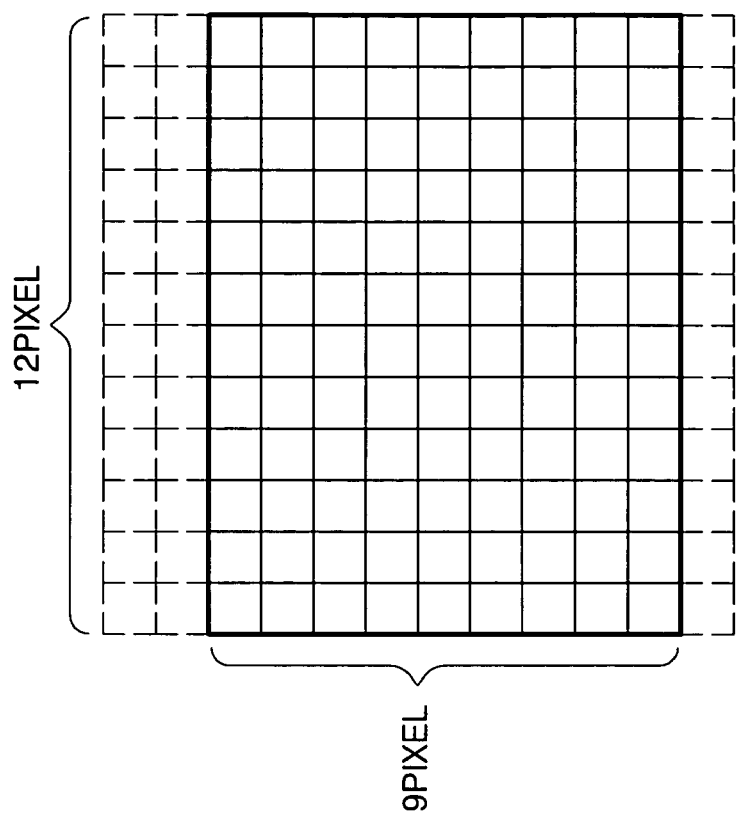
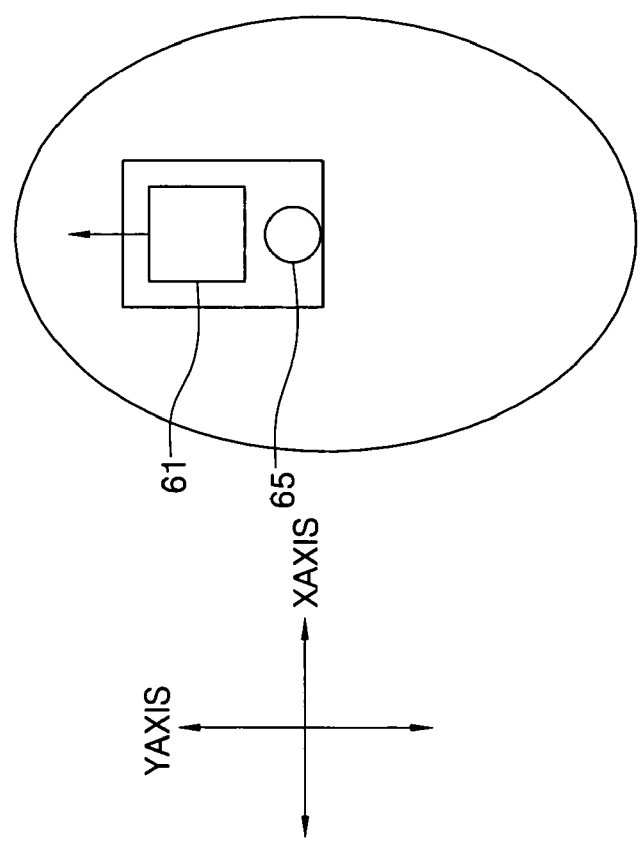

FIG. 8B
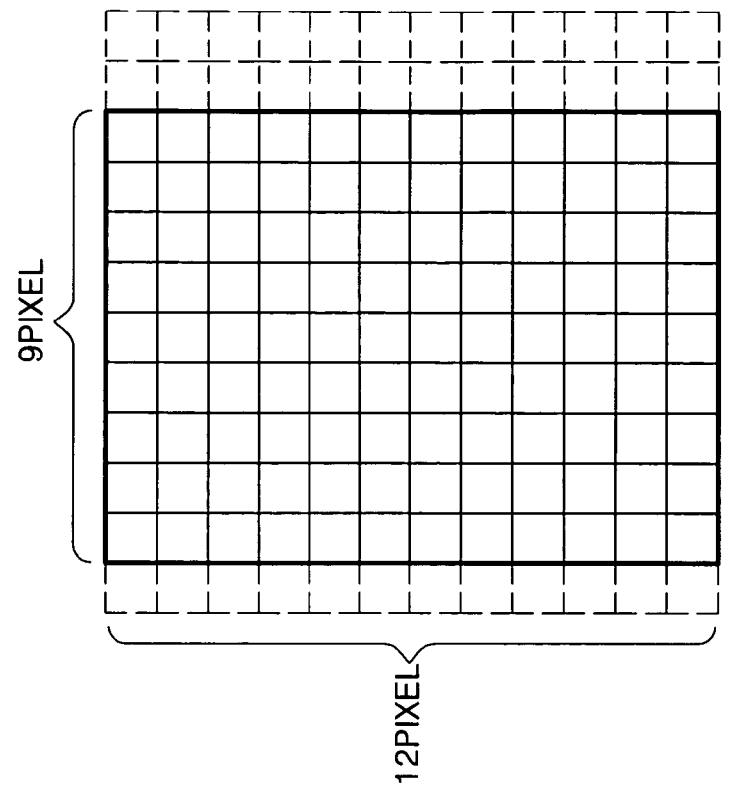
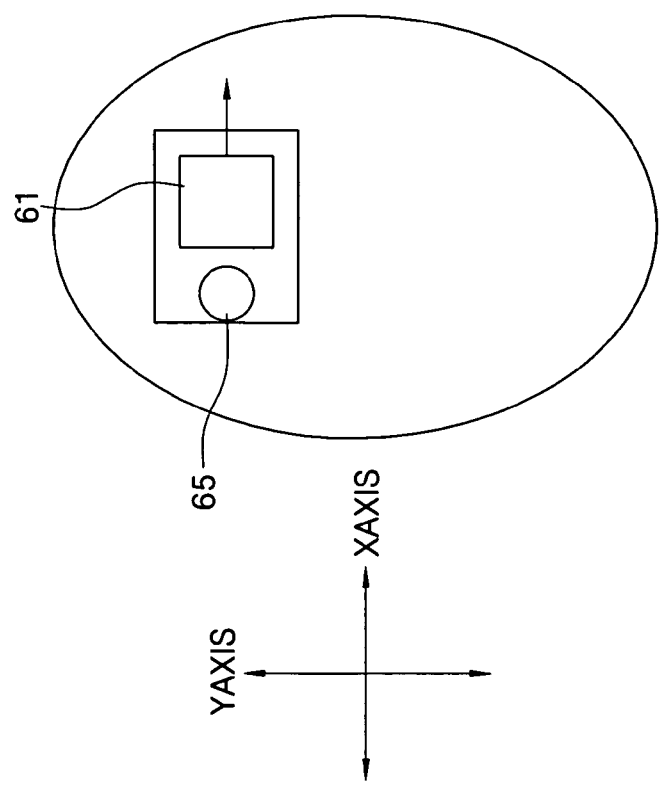

IMAGE SENSOR, OPTICAL POINTING DEVICE AND MOTION CALCULATING METHOD OF OPTICAL POINTING DEVICE

CROSS-REFERENCE TO RELATED APPLICATION

This application claims priority to and the benefit of Korean Patent Application No. 2004-16607, filed Mar. 11, 2004, the disclosure of which is incorporated herein by reference in its entirety.

BACKGROUND OF THE INVENTION

1. Field of the Invention

The present invention relates to an optical pointing device and, more particularly, to an image sensor, an optical pointing device and a motion calculating method of the optical pointing device which can calculate larger motion of the optical pointing device for an X axis direction.

2. Description of the Related Art

In general, an image sensor gets a surface image and provides an image processing device with the surface image. The image processing device which employs the image sensor includes, for example, a digital camera and an optical pointing device.

The field in which the present invention concerns is an image sensor which is employed in an optical pointing device which obtains a surface image rapidly through the image sensor and compares the currently obtained surface image with the previously obtained surface image to calculate a motion value.

FIG. 1 is a schematic view illustrating a conventional image sensor. The image sensor 1 includes a square-shaped pixel array in which the number (12) of pixels which forms an X axis and the number (12) of pixels which forms a Y axis are identical to each other. Each pixel 2 includes a photo diode 2a that an X-axis pitch X PITCH is identical to a Y-axis pitch Y PITCH, where the X-axis pitch X PITCH is identical in value to the Y-axis pitch Y PITCH. That is, each pixel has a square shape.

Each pixel 2 collects incident light while a shutter is in an ON state and generates an electrical signal corresponding to quantity of the collected light. The image sensor 1 provides an internal circuit of the optical pointing device with an image of a surface in the form of 12×12 electrical signals which are generated from the respective pixels. That is, the image sensor 1 provides the internal circuit of the optical pointing device with the image of the surface that an X-axis length "b" and a Y-axis length "a" are identical.

The internal circuit of the optical pointing device obtains the surface image collected during a current sampling period using the 12×12 electrical signals supplied from the image sensor 1 and compares it with the previously obtained surface image to thereby calculate a motion value of the optical pointing device.

FIGS. 2 and 3 are schematic views illustrating a motion calculation method of the optical pointing device which employs the image sensor of FIG. 1.

In FIG. 2, a frame 11 is a previous surface image obtained through the image sensor of FIG. 1 during a previous sampling period, and a frame 12 is a current surface image obtained during a current sampling period.

In order to calculate a motion distance during the current sampling period, the optical pointing device sets the previous frame 11 obtained during the previous sampling period as a reference frame, and sets a central area of the reference frame 11 as a reference area 11a, and sets the current frame 12 obtained during the current sampling period as a sample frame.

As shown in FIG. 3, the reference area 11a is zigzag-scanned from a left top portion (−3,3) of the sample frame 12 to a right bottom portion (3,−3) in one pixel unit to thereby calculate correlation between the reference area 11a and the sample frame 12.

A location of the sample frame 12 having the highest correlation is obtained, and a motion value of the optical pointing device is calculated using the location of the obtained sample frame 12.

In FIG. 3, the sample frame 12 has the highest correlation with the reference area 11a at a location (0,3), and thus a resultant motion value of the optical pointing device is (0,3) PIXEL.

As described above, the conventional optical pointing device gets motion by comparing the surface images continuously collected by the image sensor. An image collection rate, i.e., sampling rate is basically set to be fast in consideration of fast motion. The commercially available optical pointing device usually samples the surface image more than 1,500 times per second.

The optical pointing device is moved by a human, and the human moves more frequently in the X axis direction than in the Y axis direction and, thus a motion value of the X axis direction is greater. Thus, the sampling rate of the optical pointing device depends on the motion for the X axis direction, and so the fast sampling rate is needed as described above.

The optical pointing device and the keyboard are placed side by side for the user's convenience. In the currently available keyboard, the X axis is longer than the Y axis, and also the X axis is longer than the Y axis in the motion area of the optical pointing device for moving a cursor on the monitor screen. Therefore, in most cases, the length of the X axis on which the keyboard and the optical pointing device are placed is longer than the X axis of the monitor screen.

Further, for the user's convenience, a location of the optical pointing device protrudes to the right side of the keyboard to match the user's eyes with the center of the hand. Such keyboard and optical pointing device have more area for the X axis.

This may cause inconvenience to the user when the user uses a computer in a limited area such as a train or airplane. That is, there is a problem in that the motion area of the optical pointing device is limited.

SUMMARY OF THE INVENTION

The present invention, therefore, solves aforementioned problems associated with conventional devices by providing an image sensor which can obtain a surface image that the X axis is longer in length than the Y axis so that an optical pointing device can recognize larger motion for the X axis direction.

The present invention also provides an optical pointing device and a motion calculating method of the optical pointing device which can calculate larger motion for a certain direction by changing a motion searching range.

The present invention provides an optical pointing device and a motion calculating method of the optical pointing device which can calculate larger motion for a certain direction by changing a reference area.

In an exemplary embodiment of the present invention, an image sensor includes a pixel array for obtaining a surface image which a length of an X axis is longer than a length of a Y axis.

In another exemplary embodiment of the present invention, an optical pointing device includes: an image sensor for obtaining and providing a surface image corresponding to a motion searching range; and an image processor for determining a direction and a length of an X axis and a Y axis of the motion searching range and a reference area to continuously obtain the surface image corresponding to the direction and length of the X axis and Y axis, obtaining a reference frame and a current frame using the continuously obtained surface image, setting a certain area of the reference frame corresponding to the direction and length of the X axis and Y axis of the reference area as the reference area, and calculating a correlation between the reference area and the sample frame, to thereby calculate motion.

In yet another exemplary embodiment of the present invention, a motion calculating method of an optical pointing device includes: determining a direction and a length of an X axis and a Y axis of a motion searching range according to an arrangement structure of a light source and an image sensor; obtaining a surface image corresponding to the determined direction and length of the X axis and Y axis of the motion searching range; setting the obtained surface image as a sample frame, setting a surface image which is previously obtained and stored as a reference frame, and setting a certain area of the reference frame as a reference area; and calculating a correlation between the reference area and the sample frame to calculate a motion value.

In still another exemplary embodiment of the present invention, a motion calculating method of an optical pointing device includes: determining a direction and a length of an X axis and a Y axis of a reference area according to an arrangement structure of a light source and an image sensor; continuously obtaining a surface image through the image sensor; setting a previously obtained surface image as a reference frame and a currently obtained surface image as a sample frame, and setting a certain area of the reference frame corresponding to the determined direction and length of the X axis and Y axis of the reference area as the reference area; and calculating a correlation between the reference area and the sample frame to calculate a motion value.

BRIEF DESCRIPTION OF THE DRAWINGS

The above and other features of the present invention will be described in reference to certain exemplary embodiments thereof with reference to the attached drawings in which:

FIG. 3 is a schematic view illustrating a motion calculation method of an optical pointing device using the frames of FIG. 2;

FIG. 8a is a view illustrating a first embodiment of a method of setting a motion searching range according to an arrangement structure of the image sensor and the light source of FIG. 7;

FIG. 8b is a view illustrating a second embodiment of a method of setting a motion searching range according to an arrangement structure of the image sensor and the light source of FIG. 7;

DETAILED DESCRIPTION OF THE INVENTION

Figure 1:
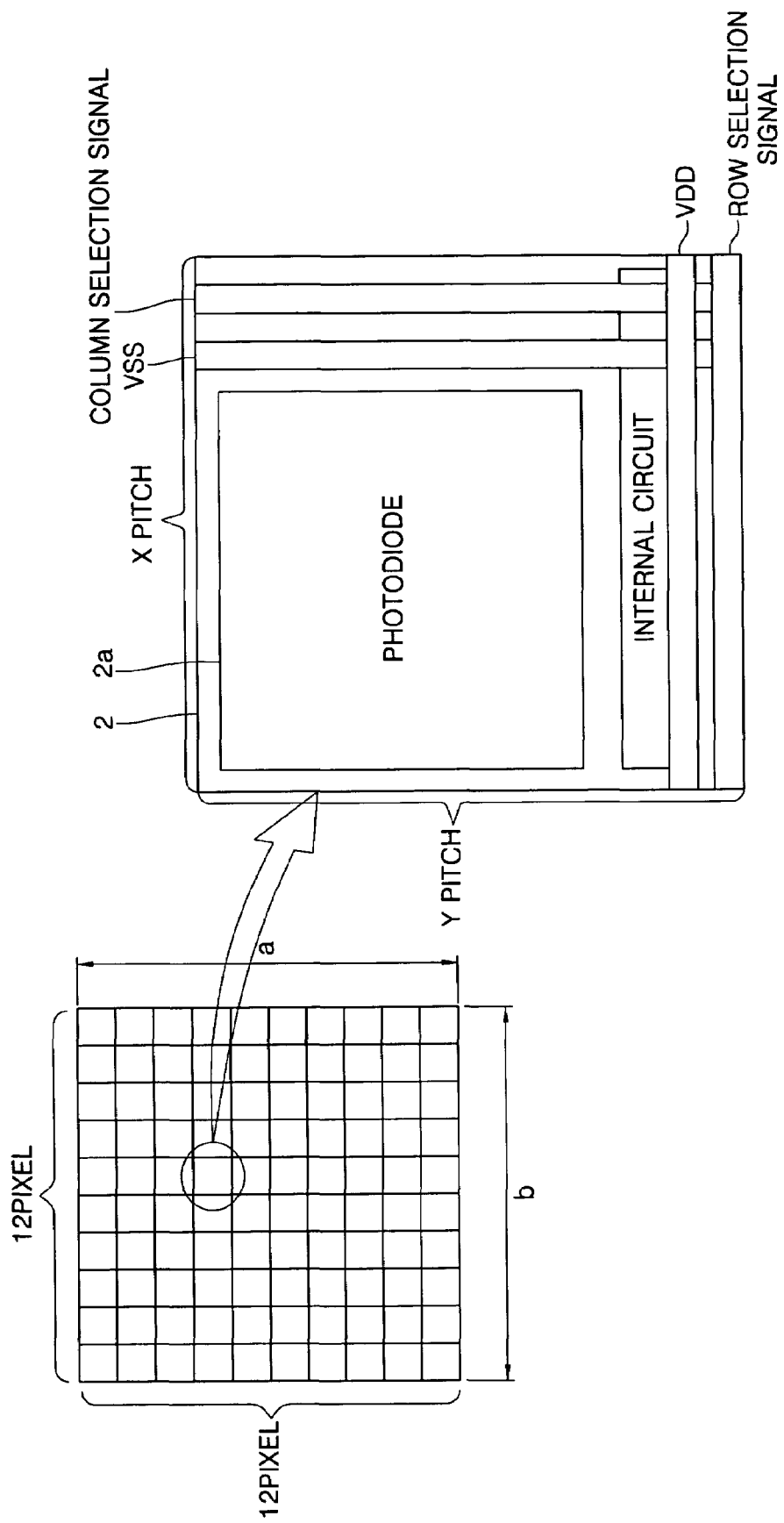
FIG. 1 is a schematic view of a conventional image sensor.
Figure 2:
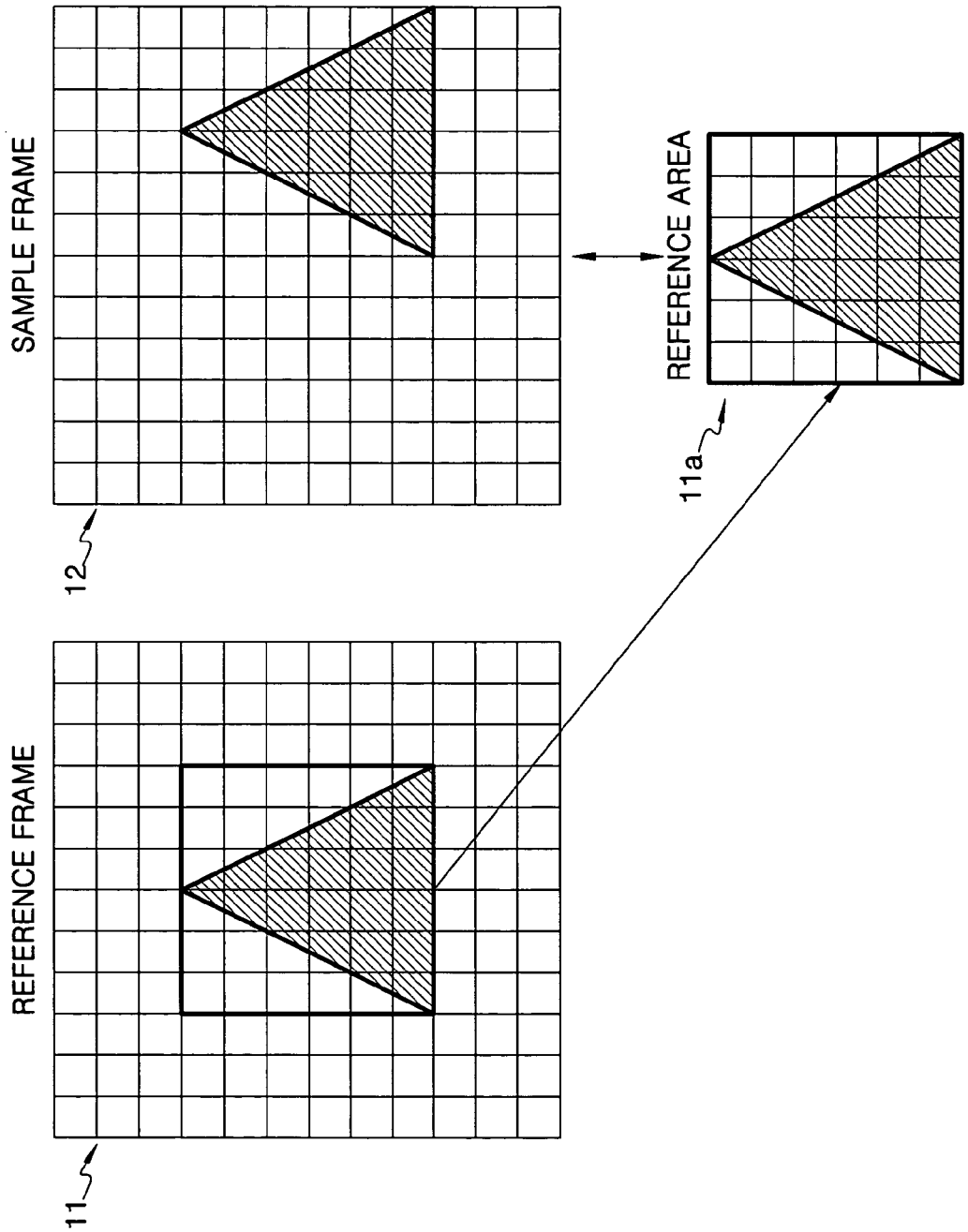
FIG. 2 is a view illustrating frames obtained through the image sensor of FIG. 1.

Reference will now be made in detail to the embodiments of the present invention, examples of which are illustrated in the accompanying drawings, wherein like reference numerals refer to the like elements throughout. The embodiments are described below in order to explain the present invention by referring to the figures.

Figure 4:
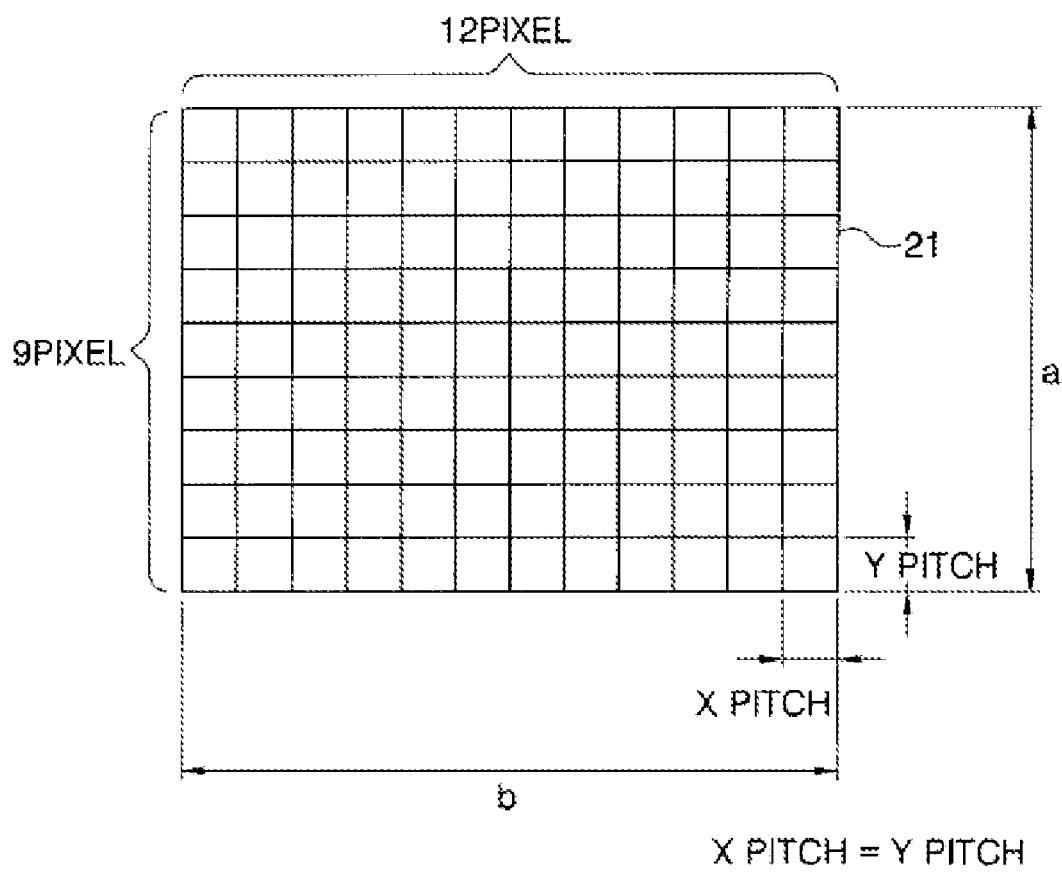
FIG. 4 is a schematic view of an image sensor according to a first embodiment of the present invention.

FIG. 4 is a schematic view of an image sensor according to a first embodiment of the present invention.

As shown in FIG. 4, the image sensor 21 includes a pixel array in which the number (12) of pixels which forms an X axis is greater than the number (9) of pixels which forms a Y axis. Here, in each pixel, X and Y pitches have the same value like FIG. 1.

The image sensor 21 obtains a surface image that "b" of the X axis is longer than length "a" of the Y axis while the shutter thereof is in an ON state, and outputs 12×9 electrical signals corresponding to each of the obtained surface image areas to an internal circuit of an optical pointing device.

Figure 5:
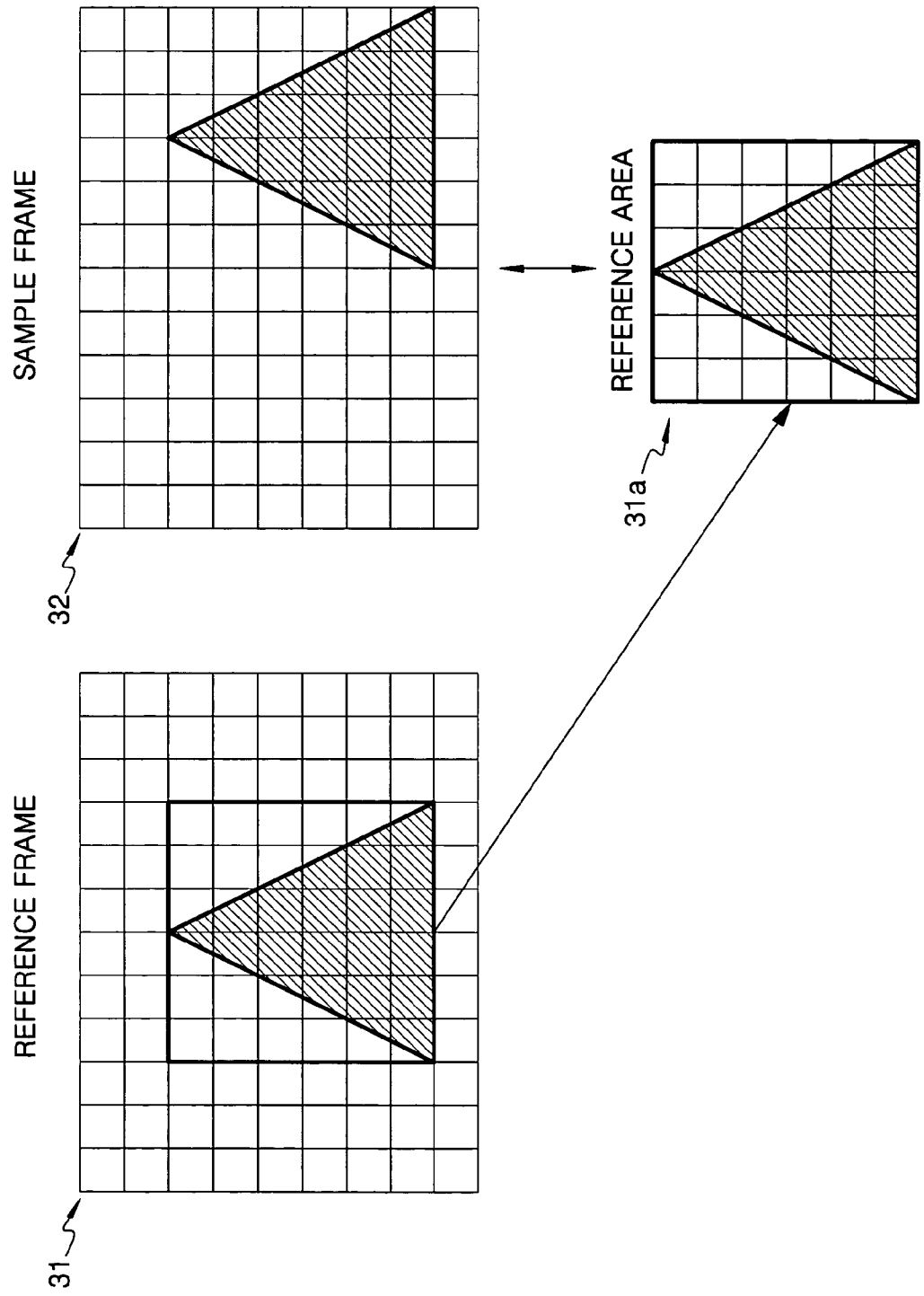
FIG. 5 is a schematic view illustrating a motion calculation method of an optical pointing device which employs the image sensor of FIG. 4.

FIG. 5 is a schematic view illustrating a motion calculation method of an optical pointing device which employs the image sensor of FIG. 4.

In FIG. 5, a frame 31 has an image of a surface obtained through the image sensor of FIG. 4 during a previous sampling period, and a frame 32 has an image of a surface obtained during a current sampling period.

The optical pointing device sets the frame 31 obtained during the previous sampling period as a reference frame, sets a central area of the reference frame 31 as a reference region 31a, and sets the frame 32 obtained during the current sampling period as a sample frame.

The reference area 31a is zigzag-scanned from a left top portion (−3,2) of the sample frame 32 to a right bottom portion (3,−1) in one pixel unit to thereby calculate correlation between the reference area 31a and the sample frame 32.

A location of the sample frame 32 having the highest correlation with the reference area 31a is obtained, and a motion value of the optical pointing device is calculated using the location (3,0) of the obtained sample frame 32.

As described above, the optical pointing device of the present invention has the image sensor which includes the pixel array that the pixel number of the X axis is greater than the pixel number of the Y axis, and so even though an image is collected at a relatively low sampling rate, larger motion of the optical pointing device for the X axis direction can be calculated.

When a lens of the image sensor is 1-magnification, the motion of the optical pointing device which can be sensed at maximum is determined by a formula of "pixel pitch×pixel number×sampling rate ".

Therefore, as the number of pixels is greater, the motion value of the optical pointing device which can be sensed is more increased. In particular, if the number of pixels which form the X axis is increased, the motion of the optical pointing device which moves in the X axis direction can be more sensed.

Figure 6:
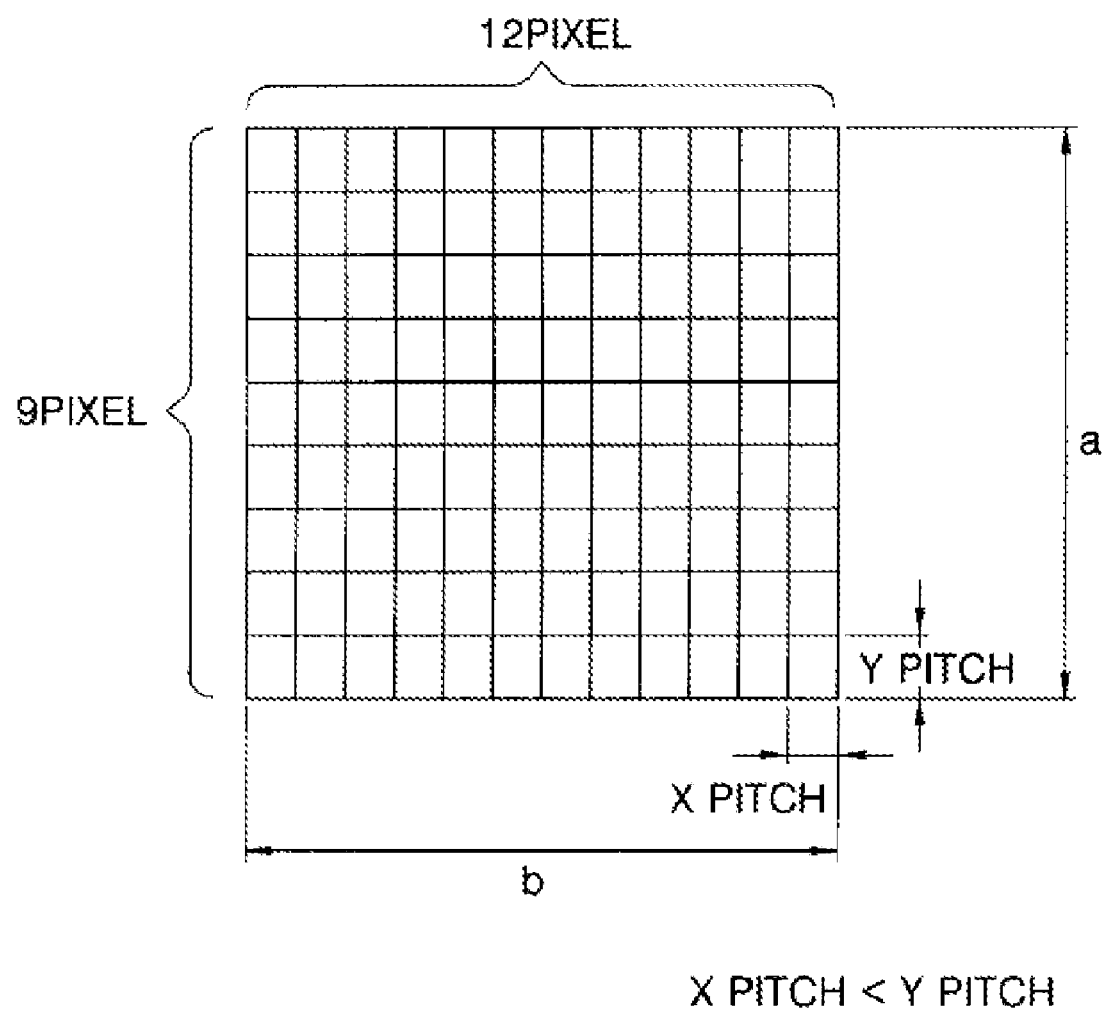
FIG. 6 is a schematic view of an image sensor according to a second embodiment of the present invention.

FIG. 6 is a schematic view of an image sensor according to a second embodiment of the present invention.

As shown in FIG. 6, the image sensor 41 is configured such that the X-axis length "b" is identical to the Y-axis length "a" but the X axis is smaller in pitch than the Y axis. The number (12) of pixels which form the X axis is greater than the number (9) of pixels which form the Y axis.

As described above, using the image sensor of FIG. 6, a resolution for the motion of the optical pointing device for the X axis direction is increased, and so even though it moves the same distance in X axis and Y axis directions respectively, the motion value for the X axis direction sensed by the optical pointing device is greater than that for the Y axis direction.

Also, an actual motion distance of the optical pointing device is smaller than a calculated motion distance.

That is, in case of moving a cursor on a monitor screen which represents a motion value of the optical pointing device with the same distance in the X axis direction and in the Y axis direction, in the motion distance of the optical pointing device that is substantially needed, a motion distance in the X axis direction is smaller than that in the Y axis direction.

This results in an effect of reducing the motion distance of the optical pointing device in the X axis direction in the situation that the motion area of the optical pointing device is limited.

Figure 7:
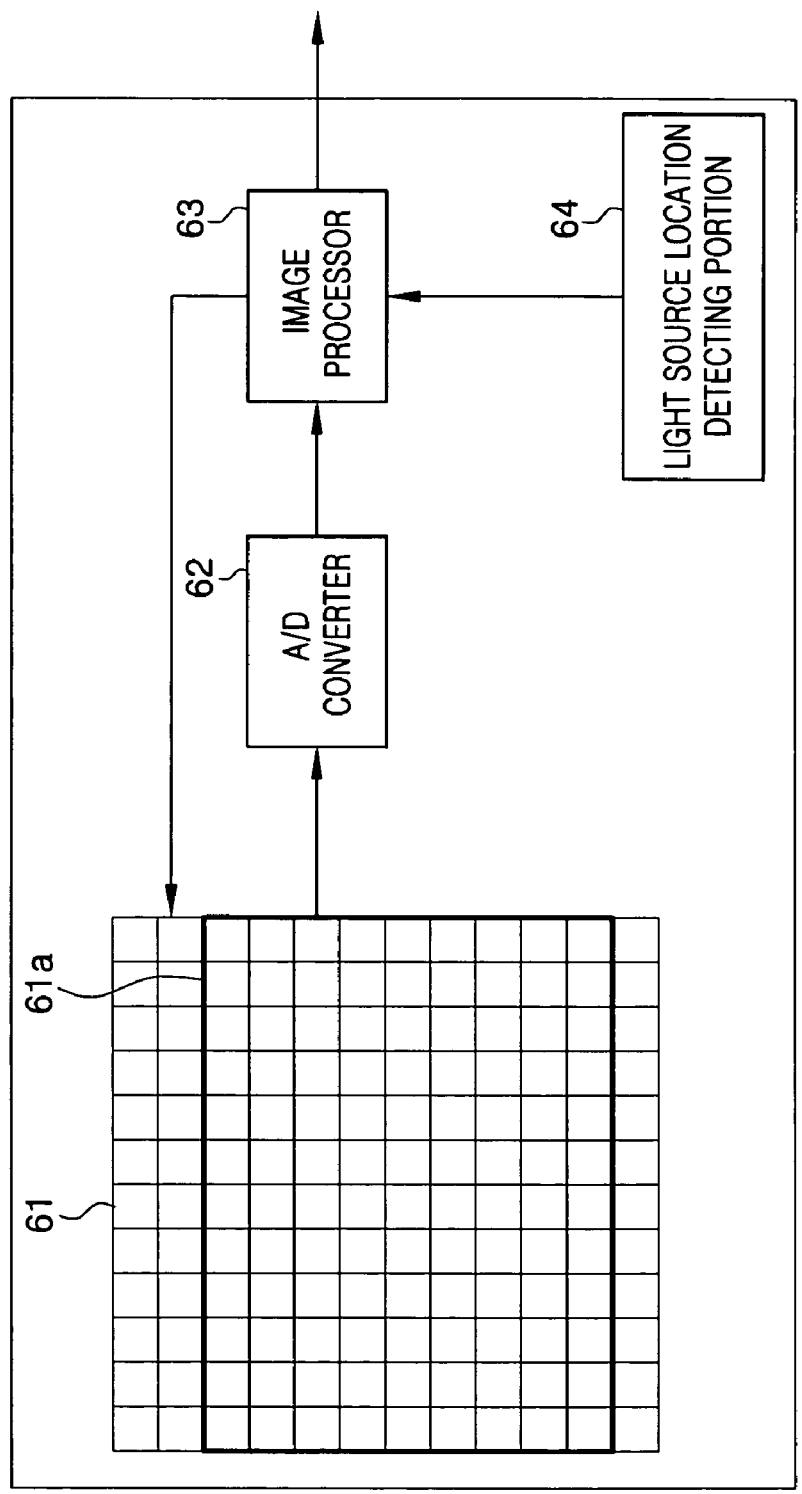
FIG. 7 is a block diagram of an optical pointing device according to the present invention.

FIG. 7 is a block diagram of an optical pointing device according to an embodiment of the present invention.

The optical pointing device of FIG. 7 limits an area to be read by the image sensor if needed, and an image sensor 61 includes a pixel array that the number (12) of pixels which form the X axis is identical to the number (12) of pixels which form the Y axis but changes a searching range 61a which looks for motion in response to a control signal from an image processor 63.

That is, the image sensor 61 activates only pixels corresponding to a certain area 61a in response to column and row selection signals and a pixel control signal which are transmitted from the image processor 63 like the conventional art, obtains a surface image through the activated pixels, and generates and outputs a plurality of electrical signals corresponding to the respective surface image areas to an A/D converter 22.

The column selection signal is a signal for activating the Y axis of the image sensor 61, and the row selection signal is a signal for activating the X axis of the image sensor 61.

The pixel control signal is a signal for determining a beginning address of the image sensor 61, and the image sensor 61 determines whether to set (−3,2) or (−3,1) as a starting point of the searching range 61a for looking for motion in response to the pixel control signal as shown in FIG. 8.

The A/D converter 62 converts each of the plurality of electrical signals supplied from the image sensor 61 into a digital signal and outputs it to the image processor 63.

The image processor 63 determines directions of the X axis and Y axis of the motion searching range in response to an output signal of a light source location detecting portion 64, and generates column and row selection signals and a pixel control signal to activate the certain area 61a of the image sensor 61 corresponding to the searching range for searching the determined motion and transmits them to the image sensor.

The image processor 63 also receives a plurality of digital signals which are provided in response to this through the A/D converter 62 from the image sensor 61, checks the surface image obtained during the current sampling period using them, and compares the surface image obtained during the previous sampling period with the surface image obtained during the current sampling period to thereby calculate a motion value of the optical pointing device.

Further, the image processor 63 may change a range of the reference area instead of the motion searching range if needed and calculate the motion value of the optical pointing device using the changed reference area. This will be described in more detail with reference to FIG. 11.

The light source location detecting portion checks, i.e., detects an arrangement structure of the image sensor 61 and a light source 65 which are attached to a bottom portion of the optical pointing device and notifies that to the image processor 63.

A method of setting the X axis and Y axis of the motion searching range and the reference area range according to the arrangement structure of the image sensor 61 and the light source 65 will be explained below.

First, if the image sensor 61 and the light source 65 are arranged to be parallel to the Y axis of the optical pointing device as shown in FIG. 8a, directions of the X axis and Y axis of the motion searching range are determined such that an actual motion direction of the optical pointing device may be identical to a recognized motion direction of the optical pointing device. Also, length (12 pixels) of the X axis of the motion searching range is longer than length (9 pixels) of the Y axis.

On the other hand, if the image sensor 61 and the light source 65 are arranged to be parallel to the X axis of the optical pointing device as shown in FIG. 8b, directions of the X axis and Y axis of the motion searching range are determined such that an actual motion direction of the optical pointing device may be perpendicular to a recognized motion direction of the optical pointing device. Also, length (9 pixels) of the X axis of the motion searching range is smaller than length (12 pixels) of the Y axis.

The X axis and Y axis in which the optical pointing device recognizes are changed, so that the optical pointing device recognizes that it moves in the Y axis direction when the optical pointing device moves in the X axis direction.

Figure 9:
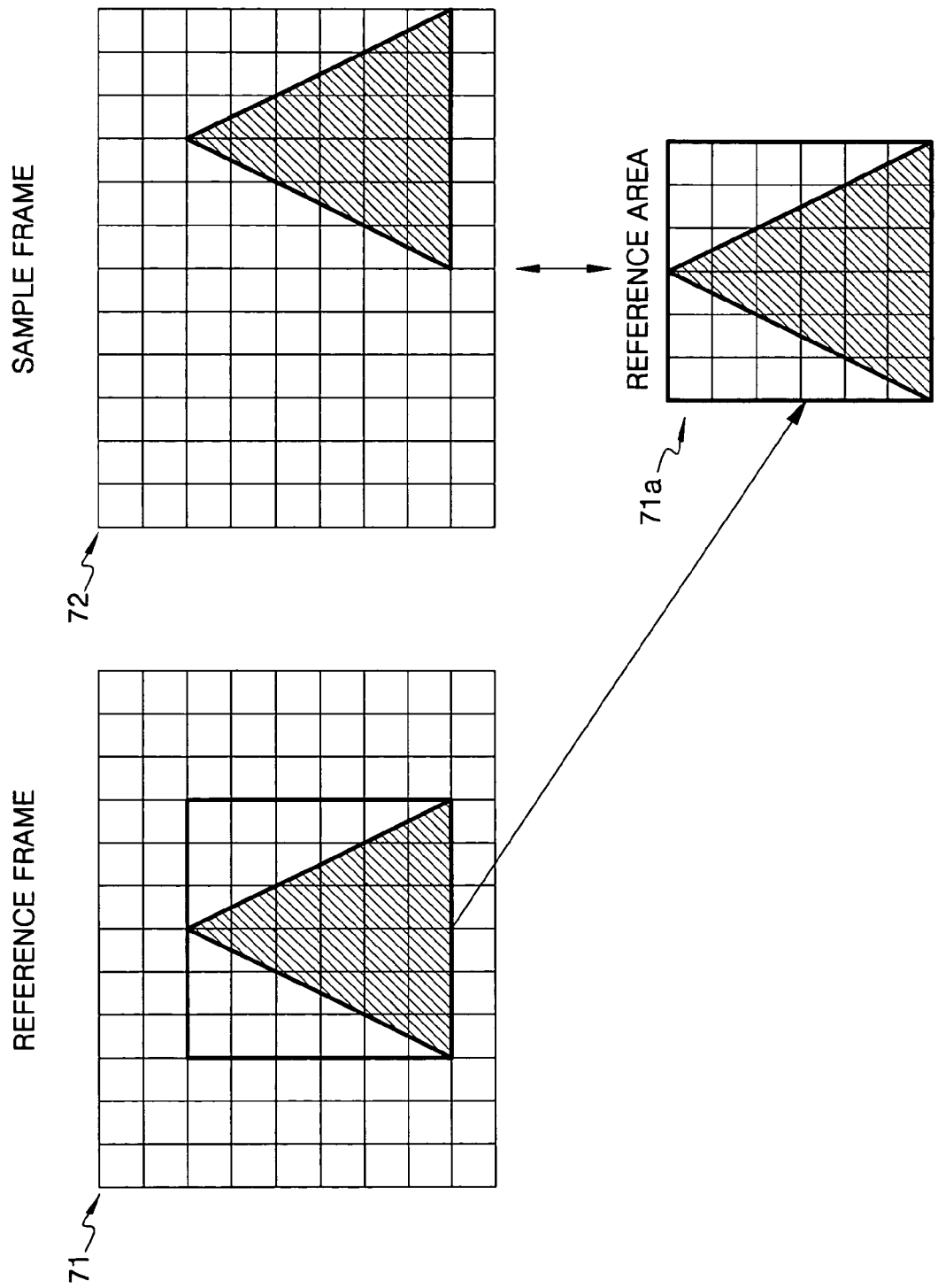
FIG. 9 is a schematic view illustrating a motion calculation method of the optical pointing device of FIG. 7 according to a first embodiment of the present invention.

FIG. 9 is a schematic view illustrating a motion calculation method of the optical pointing device of FIG. 7 according to a first embodiment of the present invention.

The motion calculation method of FIG. 9 changes the motion searching range to calculate an optical motion value. Here, let us assume that the optical pointing device has the image sensor 61 and the light source 65 which are arranged to be parallel to the Y axis of the optical pointing device as shown in FIG. 8a.

First, for the sake of an initial operation, the light source location detecting portion 64 senses the arrangement structure of the image sensor 61 and the light source 65 to notice to the image processor 63 that the image sensor 61 and the light source 65 are arranged to be parallel to the Y axis of the optical pointing device.

Therefore, the image processor 63 recognizes that an actual motion direction of the optical pointing device is identical to a recognized motion direction of the optical pointing device, and thus sets length (12 pixels) of the X axis of the searching range for searching the motion to be longer than length (9 pixels) of the Y axis. The image processor 63 generates the column and row selection signals and the pixel control signal which reflect the result and transmits them to the image sensor 61.

In response to the column and row selection signals and the pixel control signal, the image sensor 61 activates only pixels corresponding to a certain region 61a in which length of the X axis is longer than that of the Y axis When the initial operation is done as described above, the image processor 63 continuously obtains surface images 71 and 72 through the image sensor 61.

The image processor 63 sets the frame 71 obtained during the previous sampling period as a reference frame, sets a central area of the reference frame 71 as a reference area, sets the frame 72 obtained during the current sampling period as a sample frame, and compares the sample frame 72 to the reference area 71a to thereby calculate a motion value of the optical pointing device.

Figure 10:
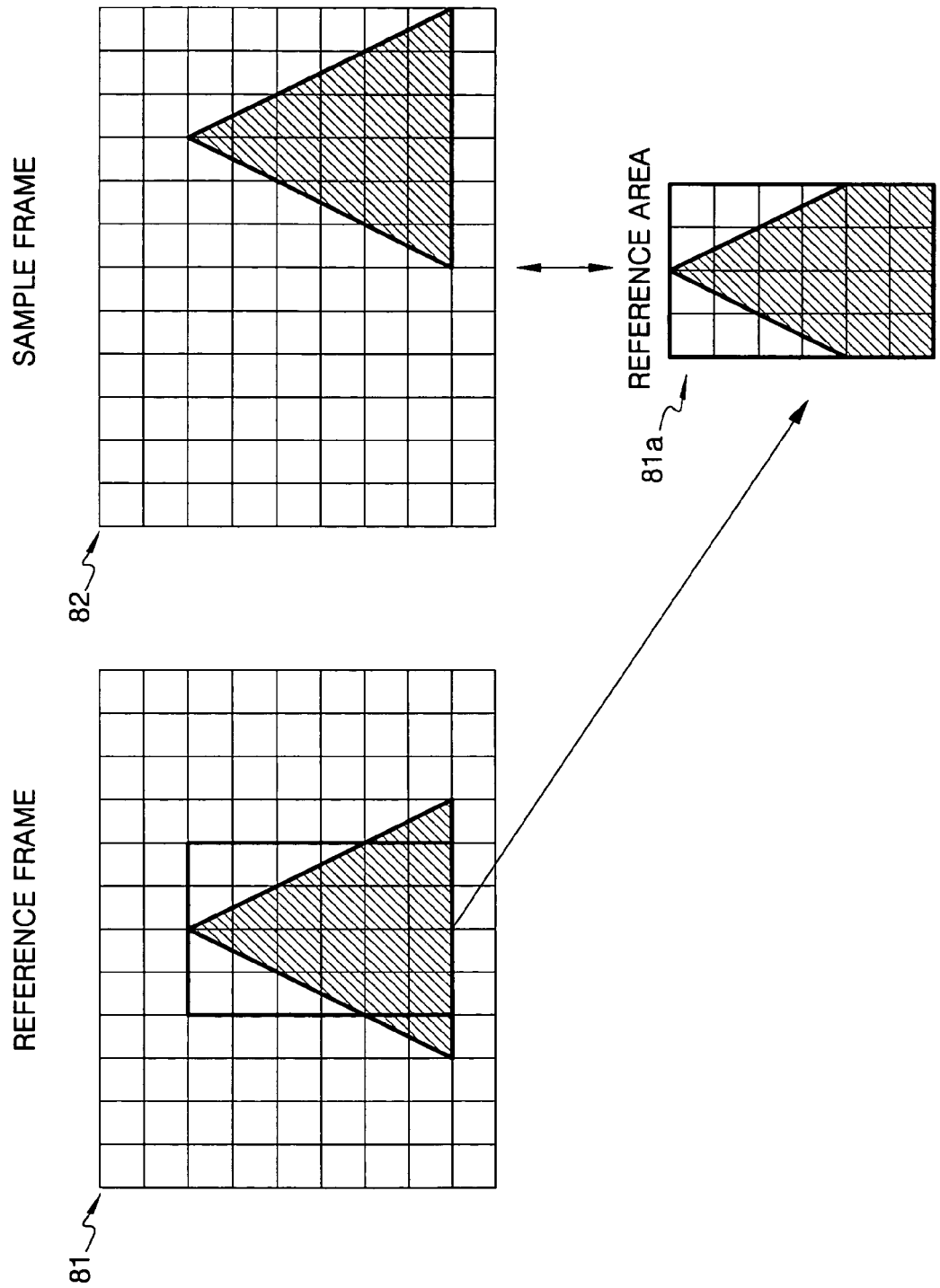
FIG. 10 is a schematic view illustrating a motion calculation method of the optical pointing device of FIG. 7 according to a second embodiment of the present invention.

FIG. 10 is a schematic view illustrating a motion calculation method of the optical pointing device of FIG. 7 according to a second embodiment of the present invention.

The motion calculation method of FIG. 10 changes a range of the reference area to calculate an optical motion value. Here, let us assume that the optical pointing device has the image sensor 61 and the light source 65 which are arranged to be parallel to the Y axis of the optical pointing device as shown in FIG. 8a.

First, during an initial operation, the light source location detecting portion 65 senses that the image sensor 61 and the light source 65 are arranged to be parallel to the Y axis of the optical pointing device, and then notices the result to the image processor 63.

Therefore, the image processor 63 recognizes that an actual motion direction of the optical pointing device is identical to a recognized motion direction of the optical pointing device, and thus sets length "c" of the X axis of the reference area range for searching the motion to be smaller than length "d" of the Y axis.

When the initial operation is done as described above, the image processor 63 continuously obtains surface images 81 and 82 through the image sensor 61.

The image processor 63 sets the frame 81 obtained during the previous sampling period as a reference frame and sets a reference area 81a in which length (4 pixels) of the X axis is smaller than length (6 pixels) of the Y axis using the reference frame 81. The image processor 63 sets the frame 82 obtained during the current sampling period as the sample frame.

Also, the image processor 63 compares the sample frame 82 with the reference area 81a in which length (4 pixels) of the X axis is smaller than length (6 pixels) of the Y axis to thereby calculate a motion value of the optical pointing device.

In the case that length (4 pixels) of the X axis is 2 pixels smaller than length (6 pixels) of the Y axis as described above, there is an advantage in that the motion value (from 4 pixel to −4 pixel) for the X axis is 2 pixels more than the motion value (from 3 pixel to −3 pixel) for the Y axis such that the optical pointing device can recognize.

Figure 11:
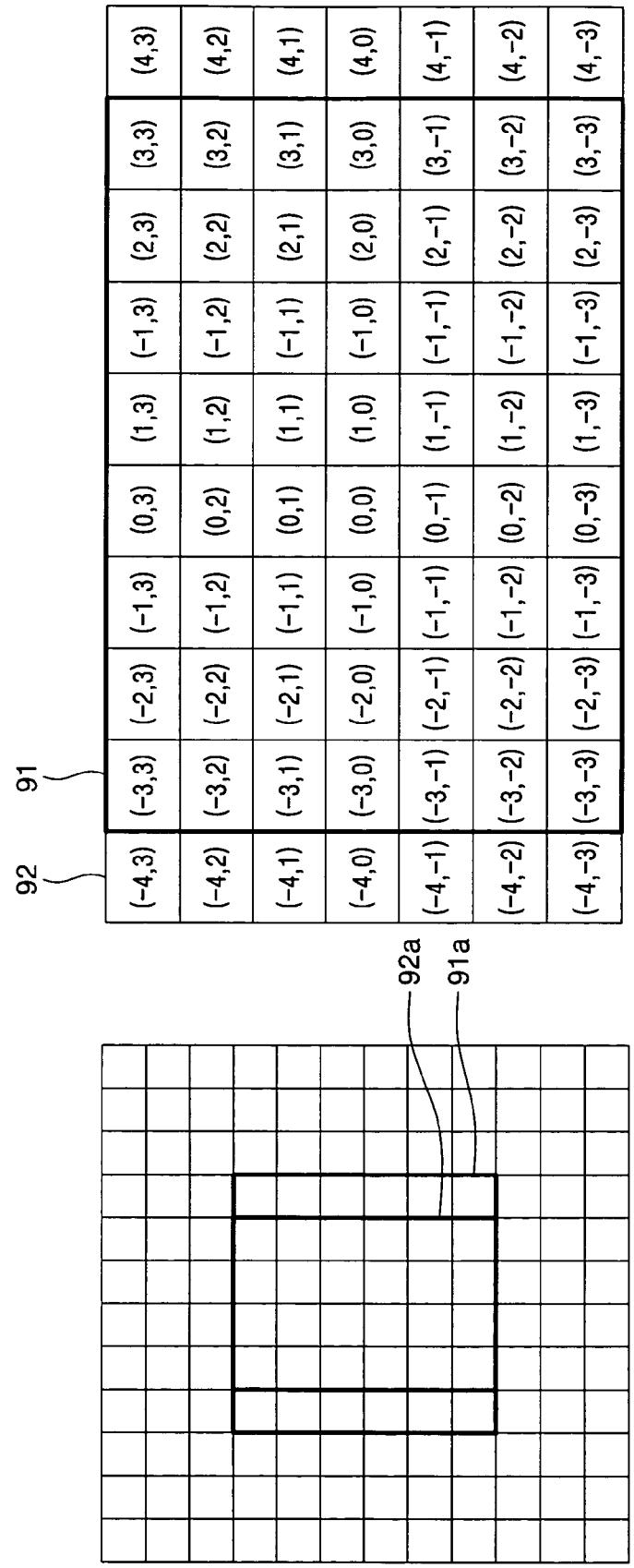
FIG. 11 is a view illustrating range of correlation according to a reference area of the present invention.

FIG. 11 is a view illustrating correlation according to a reference area of the present invention.

As shown in FIG. 11, the correlation can be described with a case 91a where length (6 pixels) of the X axis of the reference area is set to be identical to length (6 pixels) of the Y axis thereof and a case 92a where length (4 pixels) of the X axis of the reference area is set to be smaller than length (6 pixels) of the Y axis thereof.

If the sample frame is zigzag-scanned using a reference area 91a, correlation having a motion value range from (−3,3) pixel to (3,−3) pixel like 91 may be obtained, and if the sample frame is zigzag-scanned using a reference area 92a, correlation having a motion value range from (−4,3) pixel to (4,−3) pixel like 92 may be obtained.

As described above, by setting the X axis of the reference area to be 2 pixels smaller than the Y axis, there is an effect that the pixels which form the X axis of the pixel array are increased by 2 pixels.

The embodiment of the present invention has been described assuming that a ratio of the pixel number of the X axis and the pixel number of the Y axis of the image sensor and the motion searching range is 4:3 which is identical to a ratio of the current available monitor screen. But, this can be changed variously according to a user' need.

Also, in order to check the arrangement structure of the light source and the image sensor, the embodiment of the present invention provides a separate light source location detecting portion and checks the arrangement structure of the light source and the image sensor using the light source location detecting portion. However, the image processor may be configured such that it receives and stores information on the arrangement structure in advance and it operates according to the information.

As described herein before, according to the image sensor, the optical pointing device and the motion calculation method of the optical pointing device of the present invention, the image sensor can obtain the larger surface image in the X axis direction. Thus, even though the optical pointing device collects the image at a low sampling rate, there is an effect in that larger motion of the optical pointing device for the X axis direction can be calculated. This helps reduce the operating speed of the semiconductor to thereby reduce power consumption.

By getting the X pitch to be smaller than the Y pitch for each pixel of the image sensor, even though it moves the same distance in the X axis direction and the Y axis direction, the optical pointing device recognizes that the motion value for the X axis direction is greater than the motion value for the Y axis direction. Accordingly, in circumstances that motion area of the optical pointing device is limited, there is an effect in that it reduces an activity distance for the X axis of the optical pointing device.

Furthermore, by getting a ratio between length of the X axis and length of the Y axis of the motion searching range similar to a ratio of the monitor screen or getting length of the X axis of the reference area smaller than length of the Y axis, even though the image is collected at low sampling rate, there is an effect in that larger motion of the optical pointing device for the X axis direction can be calculation Although the present invention has been described with reference to certain exemplary embodiments thereof, it will be understood by those skilled in the art that a variety of modifications and variations may be made to the present invention without departing from the spirit or scope of the present invention defined in the appended claims, and their equivalents.

What is claimed is:

1. An optical pointing device comprising:
    an image sensor for obtaining and providing a surface image corresponding to a motion searching range; and
    an image processor for changing and determining a direction and a length of an X axis and a Y axis of the motion searching range and a reference area to continuously obtain the surface image corresponding to the direction and length of the X axis and Y axis, obtaining a reference frame and a sample frame using the continuously obtained surface image, setting a certain area of the reference frame corresponding to the direction and length of the X axis and Y axis of the reference area as the reference area, and calculating a correlation between the reference area and the sample frame, to thereby calculate motion, wherein the image processor changes the direction and length of the X axis and Y axis of the motion searching range and the reference area according to an arrangement structure of a light source and the image sensor; and wherein when the light source and the image sensor are parallel to a Y axis of the optical pointing device, the image processor determines the direction of the X axis and Y axis of the motion searching range such that an actual motion direction is identical to a recognized motion direction and sets the length of the X axis to be longer than the length of the Y axis, and when the light source and the image sensor are parallel to an X axis of the optical pointing device, the image processor determines the direction of the X axis and Y axis of the motion searching range such that the actual motion direction is perpendicular to the recognized motion direction and sets the length of the X axis to be shorter than the length of the Y axis.

2. An optical pointing device comprising:

an image sensor for obtaining and providing a surface image corresponding to a motion searching range; and an image processor for changing and determining a direction and a length of an X axis and a Y axis of the motion searching range and a reference area to continuously obtain the surface image corresponding to the direction and length of the X axis and Y axis, obtaining a reference frame and a sample frame using the continuously obtained surface image, setting a certain area of the reference frame corresponding to the direction and length of the X axis and Y axis of the reference area as the reference area, and calculating a correlation between the reference area and the sample frame, to thereby calculate motion, wherein the image processor changes the direction and length of the X axis and Y axis of the motion searching range and the reference area according to an arrangement structure of a light source and the image sensor; and wherein when the light source and the image sensor are parallel to a Y axis of the optical pointing device, the image processor determines the direction of the X axis and Y axis of the reference area such that an actual motion direction is identical to a recognized motion direction and sets the length of the X axis to be shorter than the length of the Y axis, and when the light source and the image sensor are parallel to an X axis of the optical pointing device, the image processor determines the direction of the X axis and Y axis of the reference area such that the actual motion direction is perpendicular to the recognized motion direction and sets the length of the X axis to be longer than the length of the Y axis.

3. A motion calculating method of an optical pointing device, comprising:

changing and determining a direction and a length of an X axis and a Y axis of a motion searching range according to an arrangement structure of a light source and an image sensor;

obtaining a surface image corresponding to the determined direction and length of the X axis and Y axis of the motion searching range;

setting the obtained surface image as a sample frame, setting a surface image which is previously obtained and stored as a reference frame, and setting a certain area of the reference frame as a reference area; and calculating a correlation between the reference area and the sample frame to calculate a motion value, wherein changing and determining the direction and length of the X axis and Y axis of the motion searching range includes:

determining the direction of the X axis and Y axis of the image sensor such that an actual motion direction is identical to a recognized motion direction and setting the length of the X axis to be longer than the length of the Y axis; and determining the direction of the X axis and Y axis of the image sensor such that the actual motion direction is perpendicular to the recognized motion direction and setting the length of the X axis to be shorter than the length of the Y axis.

4. A motion calculating method of an optical pointing device, comprising:

changing and determining a direction and a length of an X axis and a Y axis of a reference area according to an arrangement structure of a light source and an image sensor;

continuously obtaining a surface image through the image sensor;

setting a previously obtained surface image as a reference frame and a currently obtained surface image as a sample frame, and setting a certain area of the reference frame corresponding to the determined direction and length of the X axis and Y axis of the reference area as the reference area; and calculating a correlation between the reference area and the sample frame to calculate a motion value, wherein changing and determining the direction and length of the X axis and Y axis of the reference area includes:

determining the direction of the X axis and Y axis of the reference area such that an actual motion direction of the optical pointing device is identical to a recognized motion direction and setting the length of the X axis to be shorter than the length of the Y; and determining the direction of the X axis and Y axis of the reference area such that the actual motion direction is perpendicular to the recognized motion direction and setting the length of the X axis to be longer than the length of the Y axis.

* * * * *